US009561358B2

(12) United States Patent
Linden et al.

(10) Patent No.: US 9,561,358 B2
(45) Date of Patent: Feb. 7, 2017

(54) VENOUS ACCESS PORT ASSEMBLY WITH PUSH SURFACES

(75) Inventors: Christopher Linden, Allentown, PA (US); John W. Timko, Rochester Hills, MI (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 12/392,396

(22) Filed: Feb. 25, 2009

(65) Prior Publication Data
US 2009/0221976 A1    Sep. 3, 2009

Related U.S. Application Data

(60) Provisional application No. 61/067,640, filed on Feb. 29, 2008.

(51) Int. Cl.
A61M 31/00 (2006.01)
A61M 37/00 (2006.01)
A61M 39/02 (2006.01)

(52) U.S. Cl.
CPC .. *A61M 39/0208* (2013.01); *A61M 2039/0232* (2013.01)

(58) Field of Classification Search
CPC ............ A61M 2039/0232; A61M 2039/0229; A61M 2039/0208
USPC ....... 604/288.01–288.04, 751, 175, 174, 151
See application file for complete search history.

(56) References Cited

U.S. PATENT DOCUMENTS

| D44,302 S | 7/1913 | Director |
|---|---|---|
| D130,852 S | 12/1941 | Rothschild |
| 4,559,043 A | 12/1985 | Whitehouse et al. |
| 4,673,394 A | 6/1987 | Fenton, Jr. et al. |
| 4,681,560 A | 7/1987 | Schulte et al. |
| 4,692,146 A | 9/1987 | Hilger |
| 4,695,273 A | 9/1987 | Brown |
| 4,704,103 A | 11/1987 | Stoeber et al. |
| 4,710,167 A | 12/1987 | Lazorthes |
| 4,762,517 A | 8/1988 | McIntyre et al. |
| 4,772,270 A | 9/1988 | Wiita et al. |
| 4,778,452 A | 10/1988 | Moden et al. |
| 4,781,680 A | 11/1988 | Redmond et al. |

(Continued)

FOREIGN PATENT DOCUMENTS

| EP | 1238682 A2 | 3/2002 |
|---|---|---|
| FR | 2870130 | 11/2005 |

(Continued)

OTHER PUBLICATIONS

International Search Report dated May 19, 2009; PCT/US2009/035088 (4 pages).

(Continued)

*Primary Examiner* — Edelmira Bosques
(74) *Attorney, Agent, or Firm* — Buchanan Ingersoll & Rooney

(57) ABSTRACT

A venous access port assembly (10) having a housing (12), a septum (14), a discharge stem (16) at a distal end thereof for connection to a catheter (50), and an interior chamber (18). The housing includes a pair of recesses (28) along both sides thereof between the distal end and a proximal port end (24), where the recesses facilitate pushing the assembly by the practitioner into a subcutaneous pocket (104) of a patient (100) for implantation into the pocket.

18 Claims, 2 Drawing Sheets

(56) References Cited

U.S. PATENT DOCUMENTS

| | | | |
|---|---|---|---|
| 4,802,885 A | 2/1989 | Weeks et al. | |
| 4,886,501 A | 12/1989 | Johnston et al. | |
| 4,892,518 A | 1/1990 | Cupp et al. | |
| 4,904,241 A | 2/1990 | Bark | |
| 4,915,690 A | 4/1990 | Cone et al. | |
| 5,013,298 A | 5/1991 | Moden et al. | |
| 5,045,060 A | 9/1991 | Melsky et al. | |
| 5,084,015 A | 1/1992 | Moriuchi | |
| 5,108,377 A | 4/1992 | Cone et al. | |
| 5,137,529 A | 8/1992 | Watson et al. | |
| 5,167,629 A | 12/1992 | Vertenstein et al. | |
| 5,167,638 A | 12/1992 | Felix et al. | |
| 5,180,365 A | 1/1993 | Ensminger et al. | |
| 5,185,003 A | 2/1993 | Brethauer | |
| 5,207,644 A | 5/1993 | Strecker | |
| 5,213,574 A | 5/1993 | Tucker | |
| 5,263,930 A | 11/1993 | Ensminger | |
| D342,134 S | 12/1993 | Mongeon | |
| 5,281,199 A | 1/1994 | Ensminger et al. | |
| 5,281,205 A | 1/1994 | McPherson | |
| 5,318,545 A | 6/1994 | Tucker | |
| 5,356,381 A | 10/1994 | Ensminger et al. | |
| 5,360,407 A | 11/1994 | Leonard | |
| 5,387,192 A | 2/1995 | Glantz et al. | |
| 5,399,168 A | 3/1995 | Wadsworth, Jr. et al. | |
| 5,476,460 A | 12/1995 | Montalvo | |
| 5,503,630 A | 4/1996 | Ensminger et al. | |
| 5,556,381 A | 9/1996 | Ensminger et al. | |
| 5,558,641 A | 9/1996 | Glantz et al. | |
| 5,562,617 A | 10/1996 | Finch, Jr. et al. | |
| 5,593,028 A | 1/1997 | Haber et al. | |
| 5,607,393 A | 3/1997 | Ensminger et al. | |
| 5,613,945 A | 3/1997 | Cai et al. | |
| 5,620,419 A | 4/1997 | Lui et al. | |
| 5,637,102 A | 6/1997 | Tolkoff et al. | |
| 5,713,858 A | 2/1998 | Heruth et al. | |
| 5,718,682 A | 2/1998 | Tucker | |
| 5,743,873 A | 4/1998 | Cai et al. | |
| 5,792,104 A | 8/1998 | Speckman et al. | |
| 5,833,654 A * | 11/1998 | Powers et al. | 604/93.01 |
| 5,848,989 A | 12/1998 | Villani | |
| 5,951,512 A | 9/1999 | Dalton | |
| 5,989,216 A | 11/1999 | Johnson et al. | |
| 6,086,555 A | 7/2000 | Eliasen et al. | |
| 6,090,066 A | 7/2000 | Schnell | |
| 6,113,572 A | 9/2000 | Gailey et al. | |
| 6,190,352 B1 | 2/2001 | Haarala et al. | |
| 6,213,973 B1 | 4/2001 | Eliasen et al. | |
| 6,527,754 B1 * | 3/2003 | Tallarida et al. | 604/288.04 |
| 6,562,023 B1 | 5/2003 | Marrs et al. | |
| D480,942 S | 10/2003 | Ishida et al. | |
| 6,719,739 B2 | 4/2004 | Verbeek et al. | |
| 6,758,841 B2 | 7/2004 | Haarala et al. | |
| D498,894 S | 11/2004 | Gould | |
| 6,971,390 B1 | 12/2005 | Vasek et al. | |
| 6,997,914 B2 | 2/2006 | Smith et al. | |
| D518,573 S | 4/2006 | French | |
| 7,186,236 B2 | 3/2007 | Gibson et al. | |
| D546,440 S | 7/2007 | Burnside | |
| D556,153 S | 11/2007 | Burnside | |
| D562,443 S | 2/2008 | Zinn et al. | |
| D574,950 S | 8/2008 | Zawacki et al. | |
| 8,034,032 B2 | 10/2011 | Voegele et al. | |
| 2003/0130627 A1 * | 7/2003 | Smith | A61M 39/0208 604/288.04 |
| 2004/0006316 A1 | 1/2004 | Patton | |
| 2004/0204692 A1 | 10/2004 | Eliasen | |
| 2005/0075614 A1 | 4/2005 | Bunodiere et al. | |
| 2005/0077688 A1 | 4/2005 | Voegele et al. | |
| 2005/0085778 A1 | 4/2005 | Parks | |
| 2005/0171502 A1 | 8/2005 | Daly et al. | |
| 2005/0206619 A1 * | 9/2005 | McLoone et al. | 345/163 |
| 2006/0100592 A1 | 5/2006 | Eliason | |
| 2006/0116648 A1 | 6/2006 | Hamatake | |
| 2006/0184141 A1 | 8/2006 | Smith et al. | |
| 2006/0184142 A1 | 8/2006 | Schon et al. | |
| 2006/0217659 A1 | 9/2006 | Patton | |
| 2006/0217668 A1 | 9/2006 | Schulze et al. | |
| 2006/0224129 A1 | 10/2006 | Beasley et al. | |
| 2006/0247584 A1 * | 11/2006 | Sheetz et al. | 604/288.02 |
| 2006/0264898 A1 | 11/2006 | Beasley et al. | |
| 2007/0078391 A1 | 4/2007 | Wortley et al. | |
| 2007/0078416 A1 | 4/2007 | Eliason | |
| 2007/0185462 A1 | 8/2007 | Byrum | |
| 2007/0219510 A1 | 9/2007 | Zinn et al. | |
| 2007/0233017 A1 | 10/2007 | Zinn et al. | |
| 2007/0255226 A1 | 11/2007 | Tennican et al. | |
| 2007/0270770 A1 | 11/2007 | Bizup | |
| 2007/0276344 A1 | 11/2007 | Bizup | |
| 2008/0140025 A1 | 6/2008 | Sheetz et al. | |
| 2008/0319398 A1 | 12/2008 | Bizup | |

FOREIGN PATENT DOCUMENTS

| | | |
|---|---|---|
| JP | 63-38535 | 3/1988 |
| JP | 2004-350937 | 12/2004 |
| WO | 94/05351 | 3/1994 |
| WO | 97/01370 | 1/1997 |
| WO | WO97/01370 A1 | 1/1997 |
| WO | 98/55167 | 12/1998 |
| WO | WO2006096686 | 9/2006 |
| WO | WO2007082003 | 7/2007 |

OTHER PUBLICATIONS

Written Opinion dated May 19, 2009; PCT/US2009/035088 (5 pages).
PCT/US09/035088, International Preliminary Report on Patentability, dated Feb. 16, 2011, 5 pages
PCT/US09/035088, International Search Report, dated May 19, 2009, 2 pages.
PCT/US09/035088, Written Opinion, dated Aug. 31, 2010, 5 pages.
EP 09715648, Amendment, dated Apr. 23, 2011, 9 pages.
EP 09715648, Notice of Intention to Grant, dated Feb. 13, 2012, 4 pages.
Communication of a Notice of Opposition dated Apr. 23, 2013; European Application No. 09715648.3; 24 pages (with English translation, 24 pages).
Brief Communication including Affidavit of Christoph Jochum dated May 7, 2013; European Application No. 09715648.3; 3 pages. (with English translation, 3 pages).
McKee, Joy; "Future Dimensions in Vascular Access, Peripheral Implantable Ports"; Journal of Intravenous Nursing; vol. 14, No. 6, Nov./Dec. 1991; 7 pages.
"PORT-A-CATH Kathetersysteme"; dated Sep. 2006; 2 pages. (with English translation, 2 pages).
Response to Opposition; Dated: Nov. 21, 2013; 18 pages.

\* cited by examiner

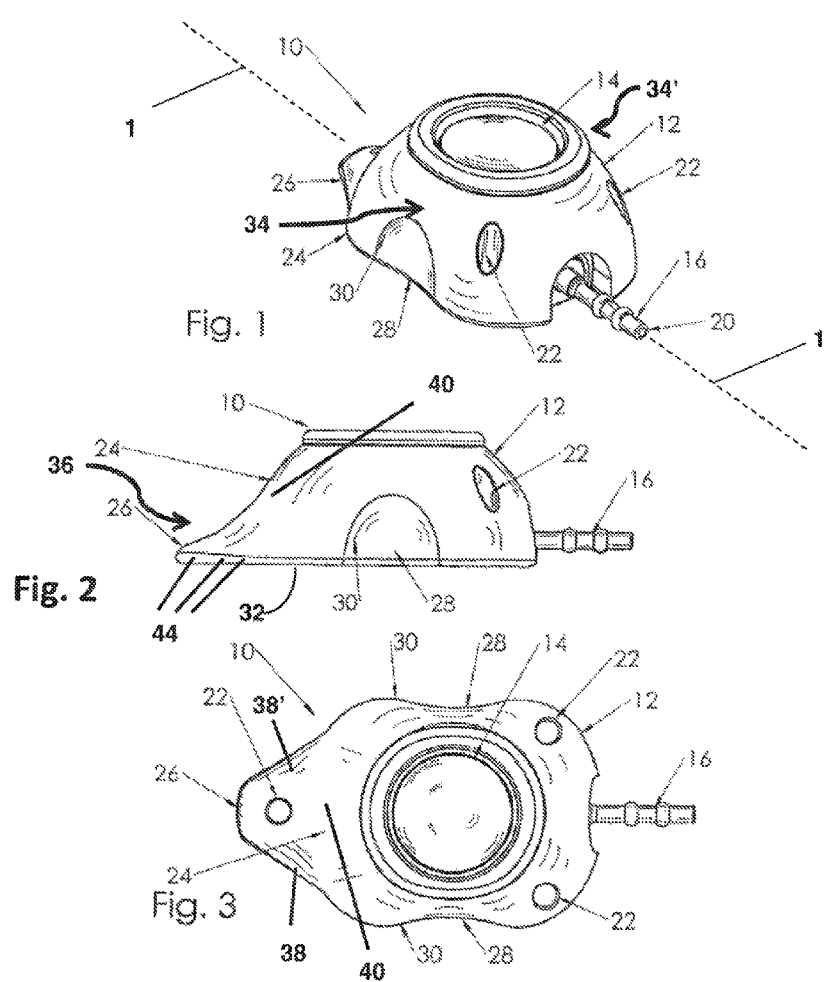

VENOUS ACCESS PORT ASSEMBLY WITH PUSH SURFACES

CROSS-REFERENCE TO RELATED APPLICATIONS

This application claims priority from U.S. Provisional Patent Application Ser. No. 61/067,640 filed Feb. 29, 2008.

FIELD OF THE INVENTION

This relates to the field of medical devices and more particularly to venous access port assemblies.

BACKGROUND OF THE INVENTION

Infusion ports for the infusion and/or withdrawal of fluids from a patient are well-known, secured to the proximal end of an implanted catheter. These ports are typically used for drug infusion or small amounts of blood withdrawal, where large flows of fluid are not required. The ports are assemblies of a needle-impenetrable housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. An example of such a port is disclosed in U.S. Patent Publication No. US 2007/0270770.

Such a venous access port assembly is implanted subcutaneously in the patient, and the catheter affixed thereto is inserted into the vasculature of the patient. For subcutaneous implanting of the assembly, a pocket is surgically created by the practitioner under the skin of the patient adjacent the incision into the blood vessel where the catheter enters the vessel. Some such ports are known to be provided with shovel-like protuberances on their proximal ends, opposite the discharge port, that assist in creating the subcutaneous pocket when urged into the incision into the skin in a direction away from the incision into the blood vessel through which the catheter enters the blood vessel.

It is desired to provide a venous access port that is easy to insert into the subcutaneous pocket.

BRIEF SUMMARY OF THE INVENTION

Briefly, the present invention is a venous access port assembly that is shaped and configured to facilitate grasping thereof in a manner to urge a proximal end of the assembly into the subcutaneous pocket. In a preferred embodiment, the housing includes a pair of large, shallow recesses on opposite sides thereof into which the thumb and forefinger of a hand of a practitioner easily fit to push the proximal end of the venous access port assembly into the pocket, with proximal surfaces of the recesses conveniently serving as push surfaces. Additional advantages are that the surfaces facilitate attachment of the catheter to the port, and, after port implantation into a patient, that the surfaces facilitate palpation and septum location.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 1 to 3 are isometric, elevation and top views of the venous access port of the present invention;

DETAILED DESCRIPTION OF THE INVENTION

Certain terminology is used herein for convenience only and is not to be taken as a limitation on the present invention. The terms "distal" and "proximal" refer, respectively, to directions closer to and away from the catheter. The terminology includes the words specifically mentioned, derivatives thereof and words of similar import. The embodiment illustrated below is not intended to be exhaustive or to limit the invention to the precise form disclosed. This embodiment is chosen and described to best explain the principle of the invention and its application and practical use and to enable others skilled in the art to best utilize the invention.

Figure 4:
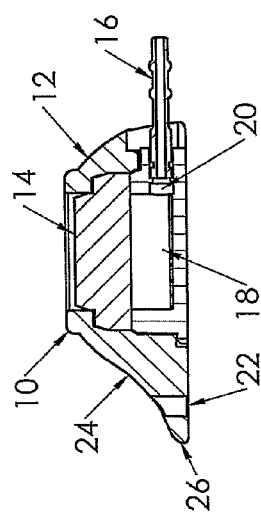
FIG. 4 is a longitudinal cross-sectional view of the port of FIGS. 1 to 3.

In accordance with the present invention, a venous access port assembly 10 of the Figures includes a housing 12, a needle-penetrable septum 14, and a discharge stem 16 onto which a catheter 50 is affixable (see FIG. 5) on a distal end of the assembly. As seen in FIGS. 1 and 3, the discharge stem 16 can define a longitudinal axis 1 of and through the port assembly 10. Further, from a top view (see FIG. 3), the port assembly 10 can be symmetrical about the longitudinal axis 1. An interior chamber 18 is seen in FIG. 4 beneath septum 14 and is in fluid communication with a passageway 20 extending to and through discharge stem 16 for eventual fluid communication with a lumen of the catheter. Housing 12 is of a needle-impenetrable material such as a plastic material like, for example, polysulfone. Septum 14 is preferably of a self-sealing material such as silicone, capable of receiving multiple needle sticks and self-sealing when the needle is withdrawn. Discharge stem 16 preferably is adapted for insertion into the proximal end of catheter 50, with a collar or barb defined along the stem's outer surface to facilitate retention of the catheter thereon. Several vertical suture holes 22 are provided through the housing for suturing of the assembly to the subcutaneous tissue of the patient after insertion of the assembly into the subcutaneous pocket (see FIG. 5).

Venous access port assembly 10 is shown to have a proximal end 24 that is shaped into a shovel-like protuberance 26 extending horizontally from the base 32 of the housing. The base 32 can be flat. The assembly further includes a pair of recesses 28 on opposing side walls 34,34' of the housing 12, with the recesses including proximal surfaces 30 that will serve as push surfaces. The proximal surface 30 of any recess 28 can include a perimeter edge as depicted in FIGS. 1-2 by the contour lines. The protuberance 26 can include a rounded tip 36 leading to a first protuberance side 38 and a second protuberance side 38', a sloped top 40, and the base 32 at the Proximal end 24 of the ort 10. The protuberance 26 can further include a rounded tip 36 leading to a sloped to 40, the sloped top 40 extending from the rounded tip 36. From a side view (see FIG. 2) both the rounded tip 36 and the sloped top 40 may extend upward from a flat base 32 of the housing 12 so as to exhibit a concave shape. From a top view (see FIG. 3) a transition from the rounded tip 36 to the sloped top 40 on each side of the port assembly 34, 34' can exhibit a concave shape. Transitions from the rounded tip 36 to the sloped top 40 and from the rounded tip 36 to the sides 34, 34' of the port assembly can be smooth. An interface 44 between the base 32 and any portion of the protuberance 26 may be continuous, in that the interface 44 is free from abrupt or pronounced undulations.

The housing 12 can further include a housing top 46 that may be an uppermost portion of the housing 12. In some embodiments, the housing top 46 immediately surrounds an entirety of a perimeter of the septum 14, as shown in FIGS. 1-3. As noted above, some embodiments include a flat base 32, which can define a flat geometric plane. The housing top 24 can be structured to form a top geometric plane. The top geometric plane can be parallel with the flat base geometric plane (see FIG. 2). In other words, the surrounding structure of the housing top 46 uppermost surface can be in a geometric plane that is parallel to the flat geometric plane of the base 32. From a top view (e.g., FIG. 3), each opposing sidewall 34,34' can define a recess 28 formed therein having a concave curvature. Each recess 28 of concave curvature may define a curved plane with an apex. A geometric tangent plane extending through each apex can be normal to the flat geometric plane of the base. In other words, the geometric tangential plane of the apex of each curved plane of each recess can be perpendicular to the flat geometric plane of the base 32. This is shown in FIGS. 1-3. Further, a portion of each opposing sidewall 34, 34' within a recess 28 may be oriented perpendicularly to the longitudinal axis 1 of the port assembly 10, as seen in FIGS. 1-3. For example, the geometric tangent plane extending through each apex can be normal to both the flat geometric plane of the base and to the longitudinal axis 1.

Some embodiments include a flat base 32, which can define a flat geometric plane. From a top view (e.g., FIG, 3), each opposing sidewall 34, 34' can define a recess 28 formed therein having a concave curvature. Each recess 28 of concave curvature may define a curved plane with an apex that is perpendicular to a flat geometric plane of the base 32. This is shown in FIGS. 1-3. Further, a portion of each opposing sidewall 34, 34' within a recess 28 may be oriented perpendicularly to the longitudinal axis 1 of the port assembly 10, as seen in FIGS. 1-3.

From the top view (e.g., FIG. 3), each opposed side wall 34, 34' can further include, along a length thereof, on each of a proximal and a distal end of a concave recess 28 formed therein, a portion of a sidewall 34,34' having convex curvature. For example, from the top view, each opposing sidewall 34, 34' can exhibit a convex curvature at an interface with a protuberance side 38, 38', then exhibit a concave curvature at the recess 28, and then exhibit a convex curvature at an interface with a distal portion of the housing 12. In other words, from the top view, each opposed sidewall 34, 34' can include convex, then concave, then convex curvature along a length thereof, from the proximal to the distal end of the housing 12. Each convex, concave, and convex curvature has a vertex, or point of inflection. As shown in FIG. 3, each inflection point of the sidewall 34 can be at a subtending location of a respective inflection point of the sidewall 34'.

As noted above, several vertical suture holes 22 may be provided through the housing for suturing of the assembly to the subcutaneous tissue of the patient after insertion of the assembly into the subcutaneous pocket. Any one suture hole 22 can be vertical with respect to the flat geometric plane of the base 32 (see FIGS. 1 and 3). In other words, any one suture hole 22 can have an axis running alone a central portion thereof that is perpendicular to the flat geometric plane of the base 32. Further, as shown in FIG. 3, a suture hole 22 can be formed within the housing 12 so as to be located at a central location between the first and second protuberance sides 38, 38'.

Figure 5:
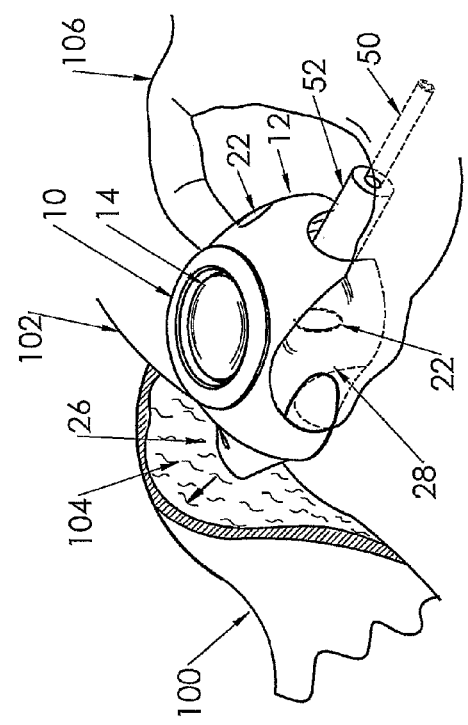
FIG. 5 is an isometric view of the port of FIGS. 1 to 4, with a catheter (in phantom) affixed to the discharge stem, a subcutaneous pocket into which the port assembly is being urged, and the port assembly being held by a practitioner's hand and being pushed into the pocket by the thumb and forefinger.

In FIG. 5, a patient 100 is receiving the venous access port assembly/catheter assembly 10,50. An incision 102 has been made into the skin of the patient, and the catheter 50 is already placed into the vasculature of the patient. A pocket 104 is being created by the practitioner at incision 102, and the port assembly 10 is being urged into pocket 104 by a practitioner 106. It can be seen that the shovel-like protuberance 26 is being urged first into the pocket and actually assists in enlarging the pocket to an appropriate snug size just large enough for containing the port assembly. The thumb and forefinger of practitioner 106 are seen placed in the recesses 28 of port assembly 10 and are urging against proximal recess surfaces 30 (FIG. 1) toward pocket 104. Additional advantages are that the surfaces facilitate attachment of the catheter to the port, and, after port implantation into a patient, that the surfaces facilitate palpation and septum location.

Other arrangements to assist the practitioner may be devised such as recesses that are angled downwardly and proximally, and/or housing surface features on both housing sides facilitating pressing of the port assembly toward and into the pocket by the thumb and forefinger of the practitioner. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A venous access port assembly, comprising:
  a housing having a base and a distal end, a proximal end, and opposed side walls between the distal and the proximal ends of the housing;
  a single septum secured to and within the housing;
  a discharge stem extending from the distal end of the housing, for connection to a catheter;
  a protuberance having a shovel shape extending from the proximal end of the housing, for subcutaneously urging the port assembly into an incision of a patient;
    wherein an outer surface of the protuberance is smooth, for urging the port assembly into the incision of the patient; and
  a single chamber located beneath the single septum and within the housing, the single chamber in fluid communication with the discharge stem, and needle accessible through the single septum;
  wherein:
    the discharge stem defines a longitudinal axis of and through the port assembly;
    from a top view, the port assembly is symmetrical about the longitudinal axis;
    the protuberance further comprising a rounded tip leading to a sloped top, the sloped top extending from the rounded tip,
    wherein:
      from a side view both the rounded tip and the sloped top extend upward from a flat base of the housing so as to exhibit a concave shape;

from a top view a transition from the rounded tip to the sloped top on each side of the port assembly exhibits a concave shape; and
transitions from the rounded tip to the sloped top and from the rounded tip to the sides of the port assembly are smooth;
an interface between the flat base and any portion of the protuberance is continuous;
from the top view, each side wall defines a single recess of concave curvature, wherein a curved plane defined by each recess has an apex that is perpendicular to a flat geometric plane of the base and each recess includes a perimeter edge.

2. The venous access port assembly of claim 1, wherein, from the top view, each opposed side wall further comprises, along a length thereof, on each of a proximal and a distal end of the concave recess, a portion of side wall having convex curvature.

3. The venous access port assembly of claim 1, wherein, from the top view, each opposed side wall includes convex, then concave, then convex curvature along a length thereof, from the proximal to the distal end of the housing, and wherein a vertex of each of the convex, then concave, then convex curvatures of a first opposing side wall is at a subtending location of a respective vertex for each of the convex, then concave, then convex curvatures of a second opposing side wall.

4. The venous access port assembly of claim 1, further comprising:
a suture hole formed within the housing, the suture hole being vertical with respect to the flat plane of the base to form a vertical suture hole located at a central location between first and second protuberance sides.

5. The venous access port assembly of claim 1, wherein, from the side elevation, each recess forms a semi-oval indentation.

6. The venous access port assembly of claim 1, wherein an uppermost portion of the housing immediately surrounds an entirety of a perimeter of the single septum and is structured to be in a geometric lane that is parallel to the flat geometric plane of the base.

7. The venous access port assembly of claim 1, wherein at least a portion of each side wall within each recess is oriented perpendicularly to the longitudinal axis.

8. A venous port assembly, comprising:
a housing having a base and a distal end, a proximal end, and opposed side walls between the distal and the proximal ends of the housing;
a single septum secured to and within the housing;
a discharge stem extending from the distal end of the housing, for connection to a catheter;
a protuberance having a shovel shape extending from the proximal end of the housing, for subcutaneously urging the port assembly into an incision of a patient, the protuberance having a first protuberance side and a second protuberance side;
wherein at least a portion of an outer surface of the protuberance, the portion including a most proximal end of the protuberance and a housing section leading to each opposing side wall, is smooth, for urging the port assembly into the incision of the patient; and
a single chamber located beneath the single septum and within the housing, the single chamber in fluid communication with the discharge stem, and needle accessible through the single septum;
wherein;
a transition from the outer surface of the protuberance to an outer surface of the base is continuous and smooth;
an interface between the base and any portion of the protuberance is continuous;
the discharge stem defines a longitudinal axis of and through the port assembly;
from a top view, the port assembly is symmetrical about the longitudinal axis;
from the top view, each side wall defines a single recess of concave curvature, wherein a curved plane defined by each recess has an apex that is perpendicular to a flat geometric plane of the base and each recess includes a perimeter edge; and
an uppermost portion of the housing immediately surrounds an entirety of a perimeter of the single septum and is structured to be in a geometric plane that is parallel to the flat geometric plane of the base.

9. The venous access port assembly of claim 8, wherein, from the top view, each opposed side wall further comprises, along a length thereof, on each of a proximal and distal end of the concave recess, a portion of side wall having convex curvature.

10. The venous access port assembly of claim 8, wherein, from the top view, each opposed side wall includes convex, then concave, then convex curvature along a length thereof, from the proximal to the distal end of the housing, and wherein a vertex of each of the convex, then concave, then convex curvatures of a first opposing side wall is at a subtending location of a respective vertex for each of the convex, then concave, then convex curvatures of a second opposing side wall.

11. The venous access port assembly of claim 8, further comprising:
a suture hole formed within the housing, the suture hole being vertical with respect to the flat plane of the base to form a vertical suture hole located at a central location between the first and second protuberance sides.

12. The venous access port assembly of claim 8, wherein, from the side elevation, each recess forms a semi-oval indentation.

13. The venous access port assembly of claim 8, wherein at least a portion of each side wall within each recess is oriented perpendicularly to the longitudinal axis.

14. A venous access port assembly, comprising:
a housing having a base and a distal end, a proximal end, and opposed side walls between the distal and the proximal ends of the housing;
a single septum secured to and within the housing;
a single discharge stem extending from the distal end of the housing, for connection to a catheter;
a protuberance having a shovel shape extending from the proximal end of the housing, for subcutaneously urging the portion assembly into an incision of a patient;
wherein at least a portion of an outer surface of the protuberance, the portion including a most proximal end of the protuberance and a housing section leading to each opposing side wall, is smooth, for urging the port assembly into the incision of the patient; and
a single chamber located beneath the single septum and within the housing, the single chamber in fluid communication with the single discharge stem, and needle accessible through the single septum;
wherein:
the discharge stem defines a longitudinal axis of and through the port assembly;

from a top view, the port assembly is symmetrical about the longitudinal axis;
the protuberance further comprising a rounded tip leading to a sloped top, the sloped top extending from the rounded tip,
wherein:
from a side view both the rounded tip and the sloped top extend upward from a flat base of the housing so as to exhibit a concave shape;
from a top view a transition from the rounded tip to the sloped top on each side of the port assembly exhibits a concave shape; and
transitions from the rounded tip to the sloped top and from the rounded tip to the sides of the port assembly are smooth;
an interface between the flat base and any portion of the protuberance is continuous;
from the top view, each side wall defines a single recess of concave curvature, each recess defining an outermost perimeter of the housing, wherein a curved plane defined by each recess has an apex that is perpendicular to a flat geometric plane of the base and each recess includes a perimeter edge; and
an uppermost portion of the housing immediately surrounds an entirety of a perimeter of the single septum and is structured to be in a geometric plane that is parallel to the flat geometric plane of the base.

15. The venous access port assembly of claim 14, further comprising:
a suture hole formed within the housing, the suture hole being vertical with respect to the flat plane of the base to form a vertical suture hole located at a central location between first and second protuberance sides.

16. The venous access port assembly of claim 14, wherein, from the side elevation, each recess forms a semi-oval indentation.

17. The venous access port assembly of claim 14, wherein at least a portion of each side wall within each recess is oriented perpendicularly to the longitudinal axis.

18. The venous access port assembly of claim 14, wherein, from the top view, each opposed side wall includes convex, then concave, then convex curvature along a length thereof, from the proximal to the distal end of the housing, and wherein a vertex of each of the convex, then concave, then convex curvatures of a first opposing side wall is at a subtending location of a respective vertex for each of the convex, then concave, then convex curvatures of a second opposing side wall.

* * * * *